(12) United States Patent
Jönsson et al.

(10) Patent No.: US 8,652,082 B2
(45) Date of Patent: Feb. 18, 2014

(54) BLOOD TREATMENT APPARATUS

(75) Inventors: Lennart Jönsson, Bjärred (SE); Olof Jansson, Vellinge (SE); Mattias Holmer, Lund (SE); Eddie Nilsson, Höör (SE)

(73) Assignee: Gambro Lundia AB, Lund (SE)

( * ) Notice: Subject to any disclaimer, the term of this patent is extended or adjusted under 35 U.S.C. 154(b) by 291 days.

(21) Appl. No.: 12/937,858

(22) PCT Filed: Apr. 14, 2009

(86) PCT No.: PCT/EP2009/054408
§ 371 (c)(1),
(2), (4) Date: Oct. 14, 2010

(87) PCT Pub. No.: WO2009/127626
PCT Pub. Date: Oct. 22, 2009

(65) Prior Publication Data
US 2011/0046535 A1    Feb. 24, 2011

Related U.S. Application Data

(60) Provisional application No. 61/044,964, filed on Apr. 15, 2008.

(30) Foreign Application Priority Data

Apr. 15, 2008 (SE) .................................. 0800862

(51) Int. Cl.
*A61M 37/00* (2006.01)

(52) U.S. Cl.
USPC ........................................... 604/6.11

(58) Field of Classification Search
USPC ........................................... 604/6.11
See application file for complete search history.

(56) References Cited

U.S. PATENT DOCUMENTS

| | | | | |
|---|---|---|---|---|
| 4,209,391 A * | 6/1980 | Lipps et al. | ................... | 210/647 |
| 4,244,816 A * | 1/1981 | Vogler et al. | ................... | 210/638 |
| 4,267,040 A * | 5/1981 | Schal | ........................... | 210/104 |
| 4,366,061 A * | 12/1982 | Papanek et al. | ............. | 210/647 |
| 4,477,342 A * | 10/1984 | Allan et al. | ..................... | 210/87 |
| 4,530,759 A * | 7/1985 | Schal | ........................... | 210/104 |
| 4,552,552 A | 11/1985 | Polaschegg et al. | | |
| 4,661,246 A * | 4/1987 | Ash | ................................. | 210/87 |
| 4,702,829 A * | 10/1987 | Polaschegg et al. | ....... | 210/195.2 |
| 5,211,849 A * | 5/1993 | Kitaevich et al. | ........... | 604/5.04 |
| 5,277,820 A * | 1/1994 | Ash | ............................... | 210/646 |
| 5,536,412 A * | 7/1996 | Ash | ............................... | 210/645 |
| 5,660,722 A * | 8/1997 | Nederlof | ........................ | 210/90 |
| 5,702,597 A * | 12/1997 | Chevallet et al. | .......... | 210/195.2 |
| 5,730,712 A * | 3/1998 | Falkvall et al. | .............. | 604/5.01 |
| 5,776,345 A * | 7/1998 | Truitt et al. | .................. | 210/645 |
| 5,817,045 A * | 10/1998 | Sever, Jr. | ..................... | 604/6.11 |
| 5,855,782 A * | 1/1999 | Falkenhagen et al. | ..... | 210/323.1 |
| 5,858,238 A * | 1/1999 | McRea et al. | ................. | 210/645 |
| 5,919,369 A * | 7/1999 | Ash | ............................... | 210/645 |
| 5,925,011 A * | 7/1999 | Faict et al. | ..................... | 604/29 |
| 6,042,784 A * | 3/2000 | Wamsiedler et al. | .......... | 422/44 |
| 6,083,187 A * | 7/2000 | Nakayama et al. | .......... | 604/6.01 |
| 6,123,859 A * | 9/2000 | Lee et al. | ..................... | 210/767 |
| 6,139,748 A * | 10/2000 | Ericson et al. | ............... | 210/646 |
| 6,280,632 B1 * | 8/2001 | Polaschegg | ................... | 210/739 |
| 6,348,162 B1 * | 2/2002 | Ash | ............................... | 252/184 |
| 6,491,656 B1 * | 12/2002 | Morris | ........................ | 604/6.09 |
| 6,495,039 B1 * | 12/2002 | Lee et al. | ..................... | 210/257.1 |
| 6,582,385 B2 * | 6/2003 | Burbank et al. | ............. | 604/5.04 |
| 6,595,943 B1 * | 7/2003 | Burbank | ...................... | 604/5.01 |
| 6,638,477 B1 * | 10/2003 | Treu et al. | ....................... | 422/44 |
| 6,645,166 B2 | 11/2003 | Scheunert et al. | | |
| 6,673,314 B1 * | 1/2004 | Burbank et al. | ............... | 422/44 |
| 6,736,972 B1 * | 5/2004 | Matson | ......................... | 210/650 |
| 6,746,606 B2 * | 6/2004 | Pfeil et al. | ..................... | 210/646 |
| 6,752,928 B2 * | 6/2004 | Pfeil et al. | ..................... | 210/646 |
| 6,780,322 B1 * | 8/2004 | Bissler et al. | ................. | 210/637 |

(Continued)

FOREIGN PATENT DOCUMENTS

DE          42 40 681 A1     6/1994
DE         197 28 071 A1     2/1999

(Continued)

OTHER PUBLICATIONS

International Search Report from the European Patent Office for International Application No. PCT/EP2009/054408 (Mail date Aug. 5, 2009).

*Primary Examiner* — Leslie Deak
*Assistant Examiner* — Guy K Townsend
(74) *Attorney, Agent, or Firm* — Nixon & Vanderhye P.C.

(57) ABSTRACT

A proposed blood treatment apparatus includes: a blood treatment unit, at least one fluid pump and at least one blood pump. The blood treatment unit is configured to receive untreated blood and fresh blood treatment fluid, and emit treated blood and used blood treatment fluid. The fluid pumps are configured to pass blood treatment fluid through the blood treatment unit. The blood pumps are configured to extract untreated blood from a blood source, pass extracted blood through the blood treatment unit and deliver treated blood to a target vessel. Additionally, at least one of the fluid pumps is configured to control the operation of at least one blood pump via the blood treatment fluid. Moreover, at least one of the blood pumps is integrated into a joint apparatus element, which includes the blood treatment unit. Thus, this blood pump and the unit may be mounted as well as be discarded jointly.

17 Claims, 11 Drawing Sheets

(56) References Cited

U.S. PATENT DOCUMENTS

| | | | |
|---|---|---|---|
| 6,787,040 B2* | 9/2004 | Radunsky et al. | 210/651 |
| 6,830,553 B1* | 12/2004 | Burbank et al. | 604/5.01 |
| 6,852,090 B2* | 2/2005 | Burbank et al. | 604/6.11 |
| 6,890,157 B2* | 5/2005 | Pfeil et al. | 417/53 |
| 6,899,693 B2 | 5/2005 | Ghelli et al. | |
| 6,918,886 B1* | 7/2005 | Baurmeister | 604/6.09 |
| 6,955,655 B2* | 10/2005 | Burbank et al. | 604/5.01 |
| 6,979,309 B2* | 12/2005 | Burbank et al. | 604/6.16 |
| 7,008,403 B1* | 3/2006 | Mallett | 604/132 |
| 7,074,332 B2* | 7/2006 | Summerton et al. | 210/646 |
| 7,112,273 B2* | 9/2006 | Weigel et al. | 210/143 |
| 7,147,613 B2* | 12/2006 | Burbank et al. | 604/5.01 |
| 7,153,286 B2* | 12/2006 | Busby et al. | 604/6.11 |
| 7,214,312 B2* | 5/2007 | Brugger et al. | 210/195.2 |
| 7,241,272 B2* | 7/2007 | Karoor et al. | 604/5.01 |
| 7,291,122 B2* | 11/2007 | Matson | 604/6.09 |
| 7,291,269 B2* | 11/2007 | Chevallet et al. | 210/650 |
| 8,029,454 B2* | 10/2011 | Kelly et al. | 604/5.01 |
| 2001/0037079 A1* | 11/2001 | Burbank et al. | 604/6.09 |
| 2002/0072718 A1* | 6/2002 | Brugger et al. | 604/246 |
| 2002/0147423 A1* | 10/2002 | Burbank et al. | 604/6.16 |
| 2003/0010718 A1* | 1/2003 | Burbank et al. | 210/651 |
| 2004/0238416 A1* | 12/2004 | Burbank et al. | 210/85 |
| 2004/0243046 A1* | 12/2004 | Brugger et al. | 604/4.01 |
| 2004/0243048 A1* | 12/2004 | Brugger et al. | 604/4.01 |
| 2004/0243050 A1* | 12/2004 | Treu et al. | 604/4.01 |
| 2004/0245161 A1* | 12/2004 | Treu et al. | 210/110 |
| 2004/0249331 A1* | 12/2004 | Burbank et al. | 604/4.01 |
| 2004/0267184 A1* | 12/2004 | Burbank et al. | 604/6.11 |
| 2005/0000868 A1* | 1/2005 | Weigel et al. | 210/90 |
| 2005/0010158 A1* | 1/2005 | Brugger et al. | 604/6.09 |
| 2005/0011823 A1* | 1/2005 | Delnevo et al. | 210/252 |
| 2005/0020959 A1* | 1/2005 | Brugger et al. | 604/4.01 |
| 2005/0020960 A1* | 1/2005 | Brugger et al. | 604/4.01 |
| 2005/0131332 A1* | 6/2005 | Kelly et al. | 604/4.01 |

FOREIGN PATENT DOCUMENTS

| | | |
|---|---|---|
| DE | 198 21 543 A1 | 11/1999 |
| EP | 0 240 101 A2 | 10/1987 |
| EP | 1 652 541 A1 | 5/2006 |
| WO | WO-93/15825 | 8/1993 |
| WO | WO 03/070314 A1 | 8/2003 |
| WO | WO-2005/046439 A2 | 5/2005 |
| WO | WO 2005/092408 A1 | 10/2005 |

* cited by examiner

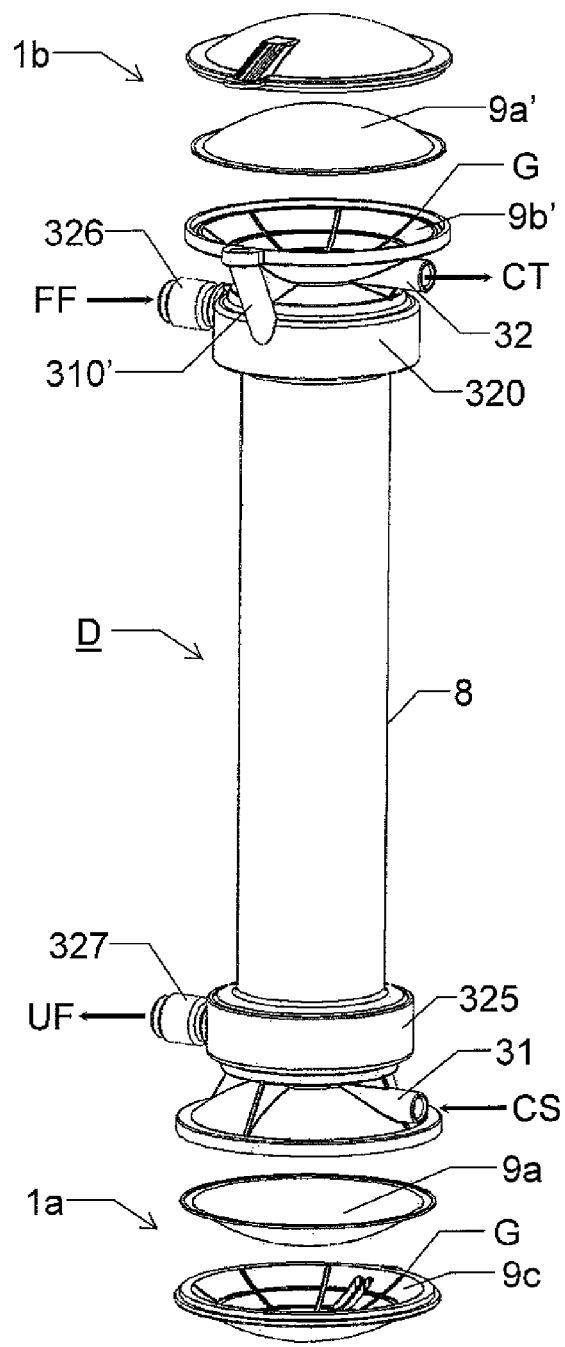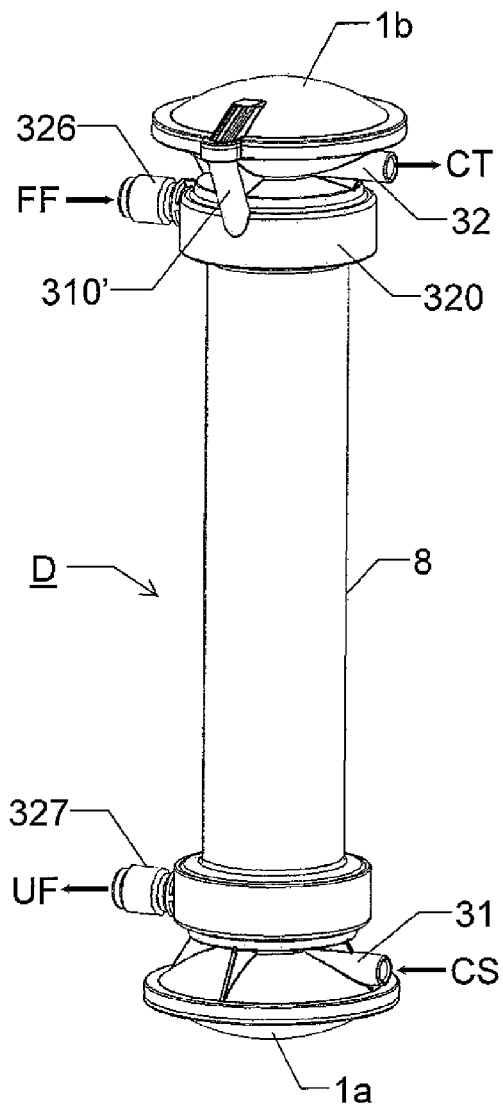
Fig. 4a
Fig. 4b

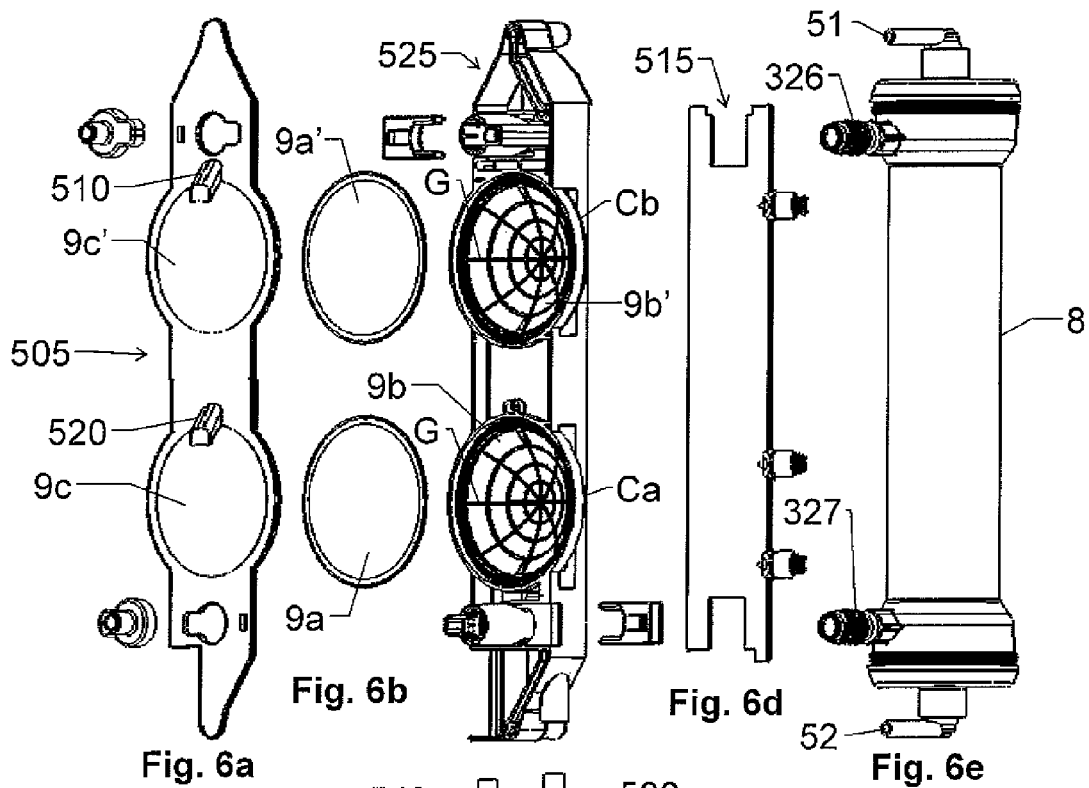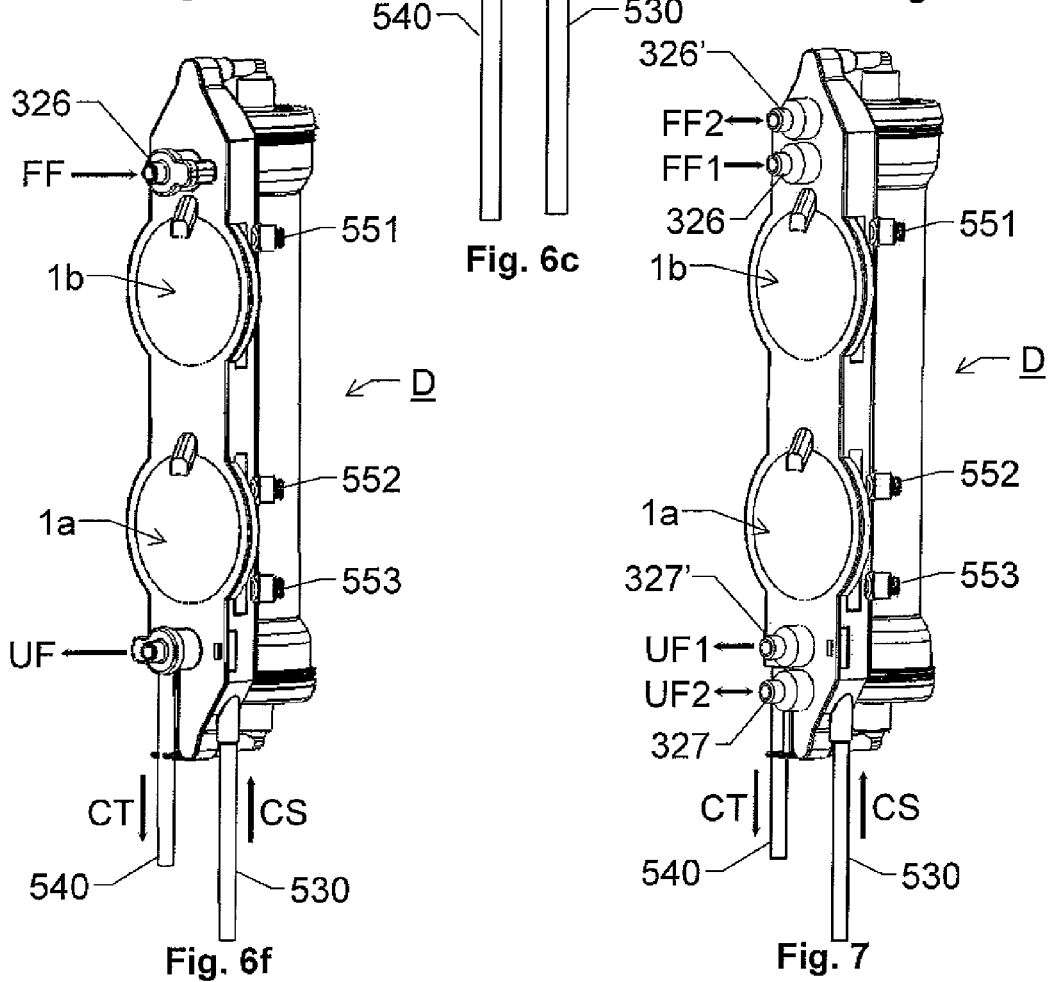

BLOOD TREATMENT APPARATUS

CROSS REFERENCE TO RELATED APPLICATIONS

This application is a national phase application based on PCT/EP2009/054408 filed Apr. 14, 2009, which claims the benefit of Swedish Patent Application No. SE 0800862-5, filed Apr. 15, 2008, and United States Provisional Application No. 61/044,964, filed Apr. 15, 2008, the contents of all of which are incorporated herein by reference.

THE BACKGROUND OF THE INVENTION AND PRIOR ART

The present invention relates generally to extracorporeal blood treatment. More particularly the invention relates to a blood treatment apparatus according to the preamble of claim 1.

A conventional single-needle blood treatment apparatus, for instance a hemodialysis system or a hemodiafiltration system, contains a dialysis fluid circuit and a blood circuit with one or two blood pumps. For patient security reasons, single-needle dialysis is advantageous in a self care setting. Namely, here, there is no risk for dislodgement of a venous needle and thereby loss of blood being pumped out unintentionally via an arterial needle. Additionally, fewer needle punctures to the patient blood access are required relative to dual-needle treatment. Generally, the single-needle system is also well suited for long lasting treatments, such as nocturnal treatments. Moreover, single-needle dialysis may be used when the patient blood access is defective.

The prior art includes a range of examples of solutions for single-needle blood treatment, as well as pump means adapted to such implementations. For example, U.S. Pat. No. 4,552,552 describes a dialysis pumping system for a single-needle dialysis apparatus with a dialyzer having blood and dialysate circuits, and wherein the blood inlets and outlets are joined by intake and outtake lines with at least one blood connection. The intake line has a driving pump and pump valves placed upstream and downstream of the blood pump. The blood pump unit has a generally stiff housing with a diaphragm therein walling off the space in the housing into a first chamber for blood and a second chamber for driving fluid that is joined up with the driving pump. A respective high and low pressure limiting valve means prevent pressure levels outside a given interval by venting the working chamber whenever the pressure falls outside predetermined threshold values.

U.S. Pat. No. 6,645,166 reveals a blood treatment device and disposable kit for a blood treatment device, e.g. a dialysis machine, which permits both single- and dual-needle operation. Here, a blood treatment unit has an inlet connected to a feed line and an outlet connected to a return line. The feed line has two parallel line branches, where a positive displacement pump is connected to a first line branch, and a negative displacement pump is connected to a second line branch. Moreover, a connection line is provided to produce a fluid connection between the outlet of the blood treatment unit and one of the two pumps. For single-needle operation, the feed and return lines are brought together and connected to a common needle.

U.S. Pat. No. 6,899,693 discloses a compact pulsating pumping unit including means suitable to draw blood from an intake connector in order to send it to an outlet connector. Said means are contained in an enclosure provided with valves connected to the inlet and the outlet. An elastic membrane here separates the enclosure into two domes. This allows a working fluid to act on one side of the membrane, such that the membrane acts on blood located on the opposite side. The membrane thereby controls the operation of an inlet valve and an outlet valve, such that blood is moved into respective out from a pumping chamber.

Although the above solutions may have specific beneficial characteristics, they fail to provide an overall optimal fluid flow in a blood treatment apparatus. Moreover, operating the apparatus requires pressure measurements on the blood side. Hence, the design of the apparatus is compelled to be relatively intricate, and handling the apparatus becomes impractical. This, in turn, renders the apparatus unsuitable for a self care setting, where convenient and fail-safe handling is very important. Furthermore, blood pressure measurements on the blood side are problematic due to the potential risk of infection and contamination of the blood via the pressure measuring means, e.g. due to blood residuals from earlier treatments.

SUMMARY OF THE INVENTION

The object of the present invention is therefore to alleviate the above problems and provide an efficient and yet uncomplicated blood treatment solution, which is well adapted for a home/self treatment environment.

According to the invention, the object is achieved by the apparatus as initially described, wherein at least one of the at least one fluid pump is configured to control the operation of at least one of the at least one blood pump via the blood treatment fluid. Moreover, at least one of the at least one blood pump is integrated into a joint apparatus element that includes the blood treatment unit.

The proposed blood treatment apparatus is advantageous because it allows an uncomplicated overall design, which is safe regarding the risk of blood infection/contamination. Namely, all blood pressure measurements can be made on the fluid side. Furthermore, the entire joint apparatus element may be made disposable. This facilitates the handling of the apparatus considerably relative to the known solutions.

According to one embodiment of the invention, each of the at least one blood pump includes a pumping chamber and a flexible member separating the pumping chamber into a first accumulation container and a second accumulation container. The flexible member is movable within the pumping chamber so as to vary a volume relationship between the first and second accumulation containers. The second accumulation container is configured to receive an amount of working fluid to act on the flexible member and thus pump blood from the first accumulation container. Moreover, the at least one fluid pump and the at least one blood pump are arranged, such that the blood treatment fluid constitutes the working fluid for the at least one blood pump. Thus, the fluid pump controls the operation of the blood pump via the blood treatment fluid.

According to another embodiment of the invention, the apparatus includes two blood pumps, and both these pumps are integrated into the joint apparatus element. Naturally, this is advantageous because the handling of the apparatus is thereby further facilitated.

According to yet another embodiment of the invention, each of the at least one blood pump is configured to be in fluid connection with the treatment unit throughout an entire treatment of an amount of blood from the blood source. Such a blood flow is desirable from an efficiency point-of-view.

According to still another embodiment of the invention, each of the at least one fluid pump is configured to be in fluid connection with the treatment unit throughout an entire treatment of an amount of blood from the blood source. Analogously, such a blood treatment fluid flow is likewise desirable from an efficiency point-of-view.

According to a further embodiment of the invention, the apparatus includes first and second blood conduits and at least one needle connector. The first blood conduit is configured to be connected to the blood source, the second blood conduit is configured to be connected to the target vessel, and the at least one needle connector is/are configured to connect the first and second blood conduits to at least one needle. Thereby, the first and second blood conduits may be conveniently connected to the blood source and target vessel respectively.

According to another embodiment of the invention, the first blood conduit includes a primary safeguard module configured to check at least one quality parameter of the treated blood delivered to the target vessel. For example the primary safeguard module may include an air bubble detector adapted to detect any undesired gas bubbles in the treated blood being delivered to the target vessel. The primary safeguard module may also/alternatively include a priming fluid detector means adapted to detect any priming fluid being passed through the apparatus. Hence, unwanted substances can be prevented from reaching the target vessel, e.g. represented by a patient's blood system.

According to yet another embodiment of the invention, the second blood conduit includes a secondary safeguard module configured to check at least one quality parameter of the untreated blood received from the blood source. Thereby, also a certain quality of the blood entering the apparatus can be guaranteed. However, mainly, the secondary safeguard module is advantageous in case the apparatus unintentionally comes to pass blood in the opposite direction (i.e. back into the blood source, for instance a patient's blood system), various unwanted substances can be prevented from reaching the blood source.

According to further embodiments of the invention, the joint apparatus element includes a body module that has an essentially cylindrical outline with a central length axis. Here, the blood pumps in the joint apparatus element are arranged at end segments of the blood treatment unit, such that one or more blood pumps are located essentially symmetrically with respect to the central length axis; and/or one or more blood pumps are arranged on a side surface of the blood treatment unit, such that each of these blood pumps is arranged essentially asymmetrically with respect to the central length axis. Namely, depending on the general design of the blood treatment apparatus different blood pump locations may be advantageous in terms of compactness, manufacturing efficiency and/or consumption of material.

Although the proposed solution is particularly suitable for self care treatment, the invention is equally well applicable to incenter intermittent care, daily/nocturnal dialysis and intensive/continuous care. Clearly, the invention is applicable to dual-needle implementations. However, the proposed solution is especially advantageous for blood treatment in the form of single-needle hemodialysis or hemodiafiltration. Further advantages, beneficial features and applications of the present invention will be apparent from the following description and the dependent claims.

BRIEF DESCRIPTION OF THE DRAWINGS

The present invention is now to be explained more closely by means of embodiments, which are disclosed as examples, and with reference to the attached drawings.

Figure 3:
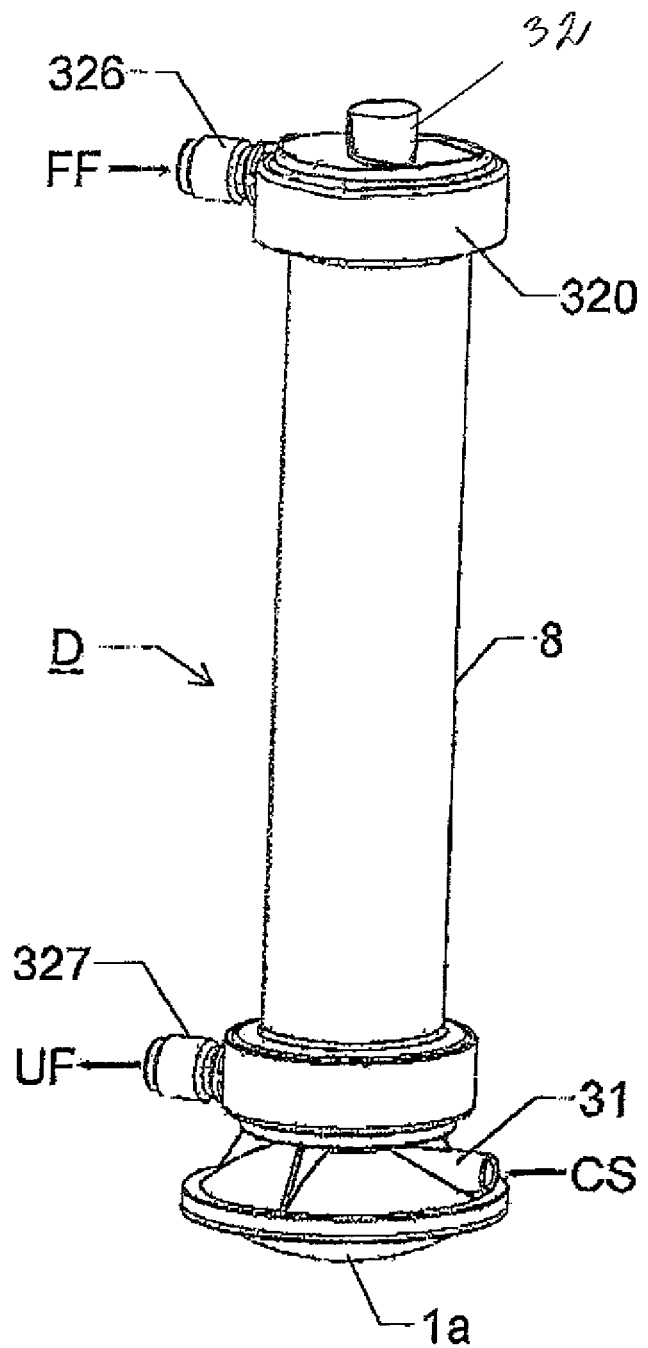
Figures 5A, 5B:
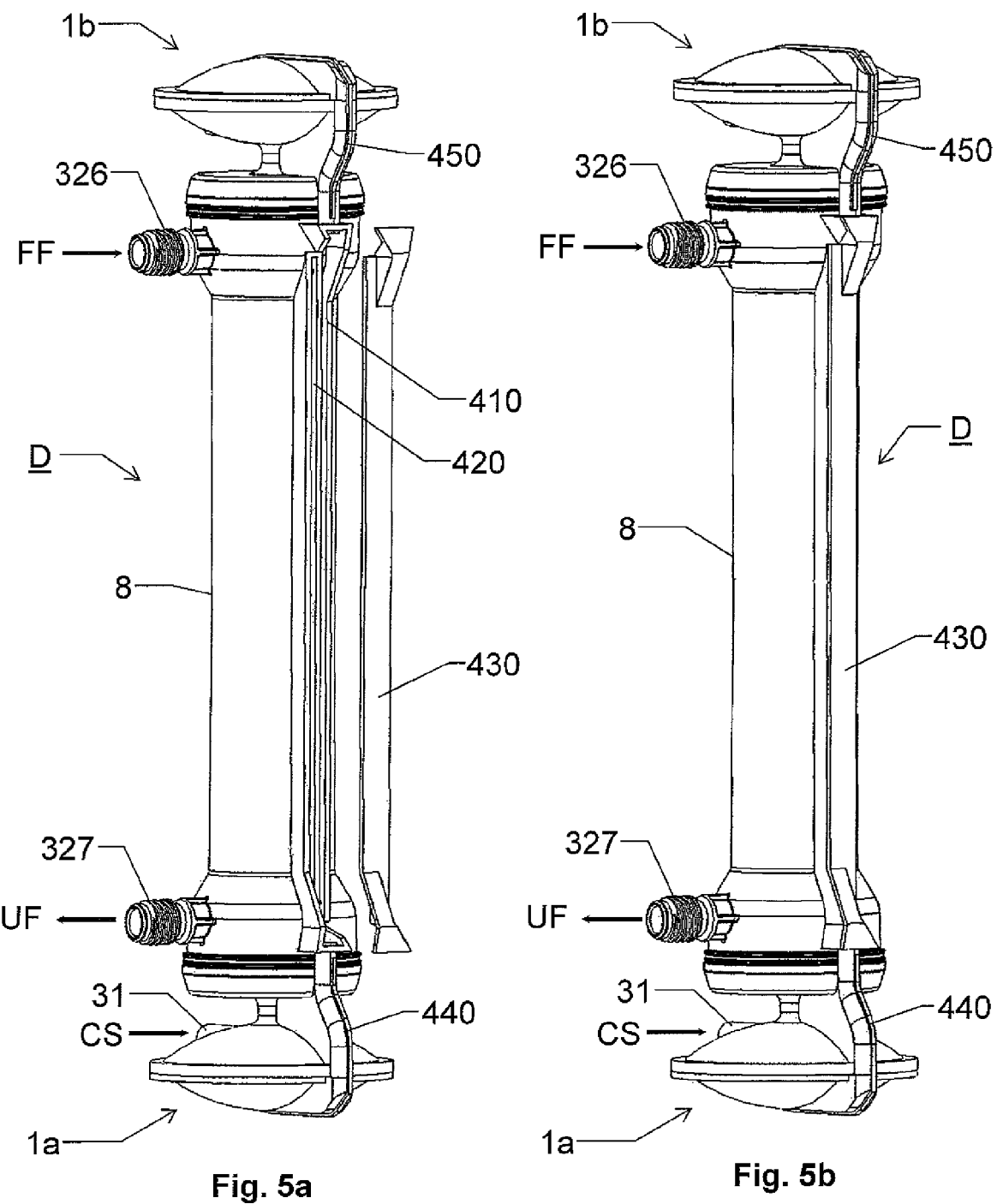
Figure 8:
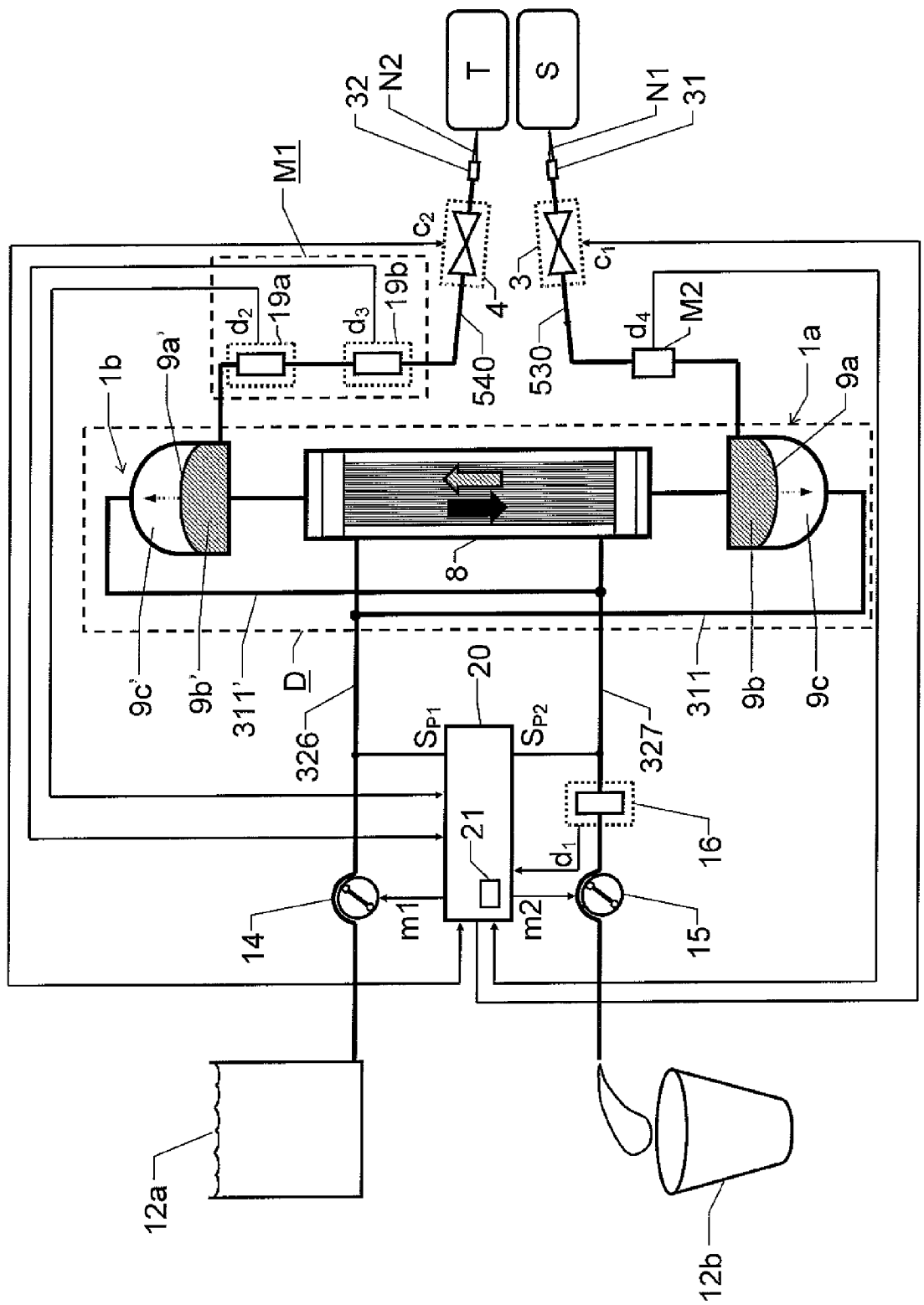

Tables 1-2 illustrate blood extraction and blood return phases relative to when blood treatment fluid respective blood is passed through the blood treatment unit in the different embodiments of the invention;

FIG. 3 shows a perspective view of the proposed joint apparatus element according to a first design alternative suitable for the apparatus according to the first embodiment of the invention;

FIGS. 4a-b show perspective views of the proposed joint apparatus element according to a second design alternative suitable for the apparatus according to the second embodiment of the invention;

FIGS. 5a-b show perspective views of the proposed joint apparatus element according to a third design alternative;

FIGS. 6a-f show perspective views of the proposed joint apparatus element according to a fourth design alternative; and FIG. 7 shows a perspective view of the proposed joint apparatus element according to a fifth design alternative; and FIG. 8 shows a block diagram over a blood treatment apparatus according to a third embodiment of the invention in which the joint apparatus element according to the third design alternative may be used.

Figure 9A:
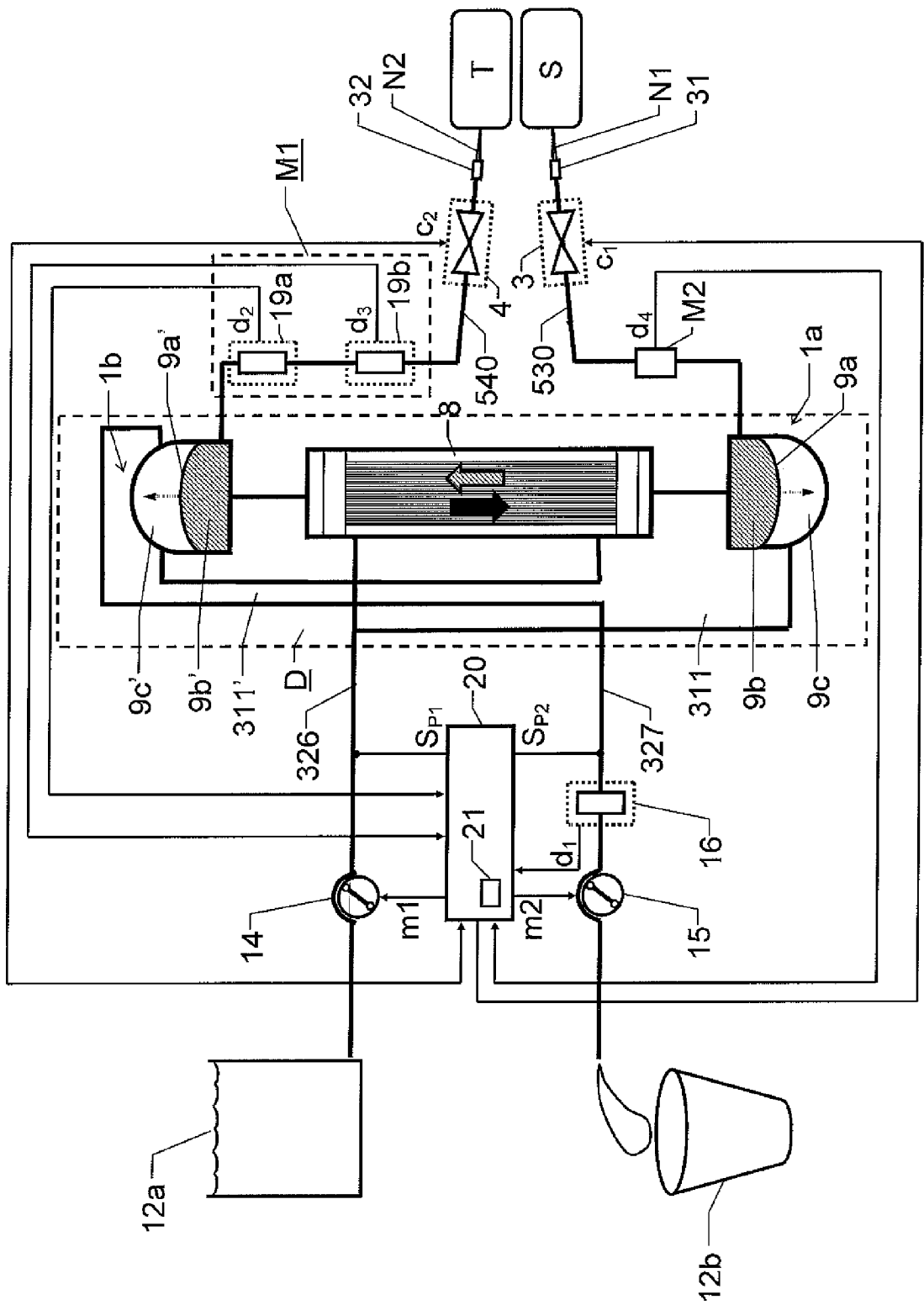
Figure 9B:
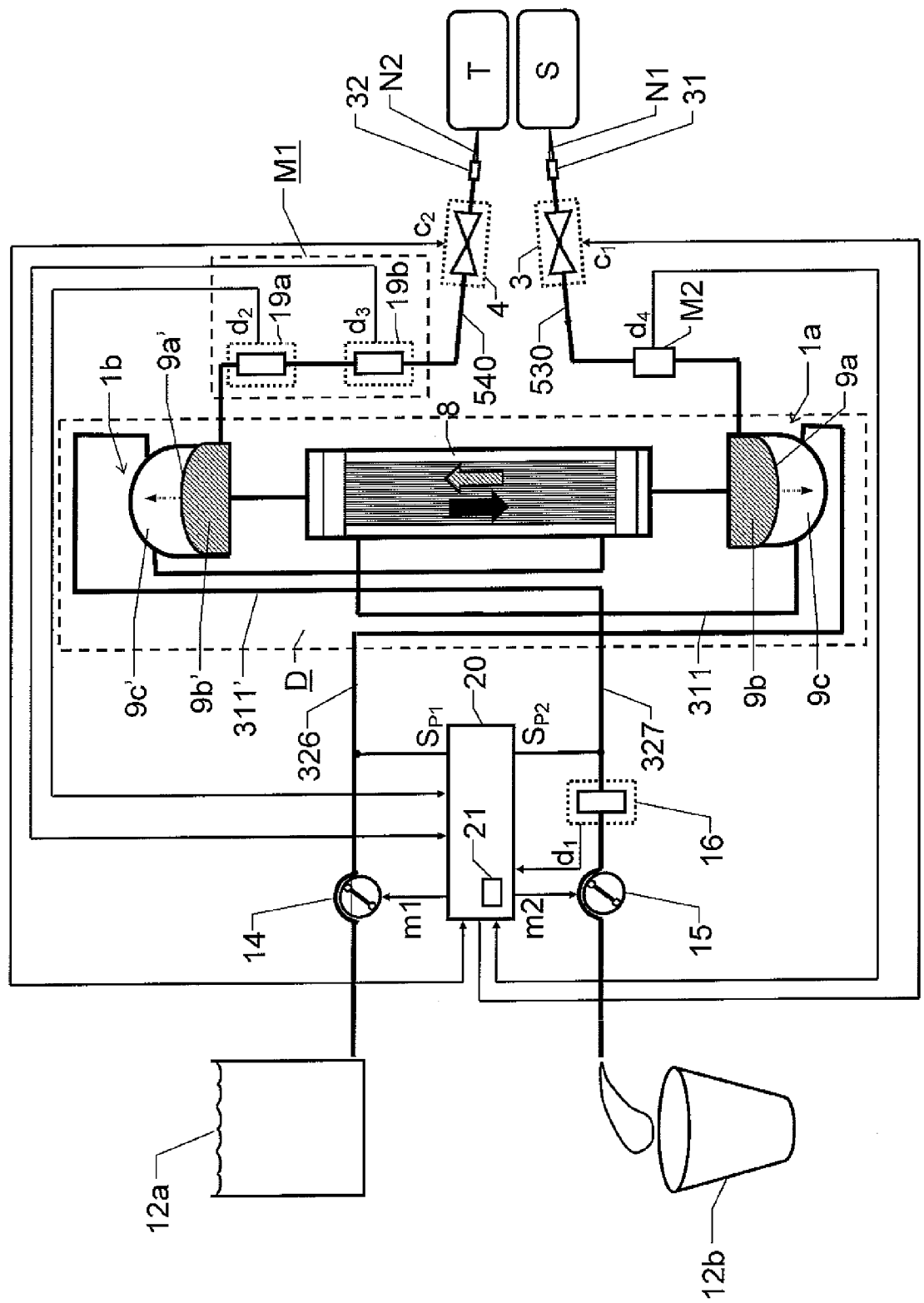

FIGS. 9a-b show block diagrams over a blood treatment apparatus according to a fourth and a fifth embodiment of the invention.

DESCRIPTION OF EMBODIMENTS OF THE INVENTION

Figure 1A:
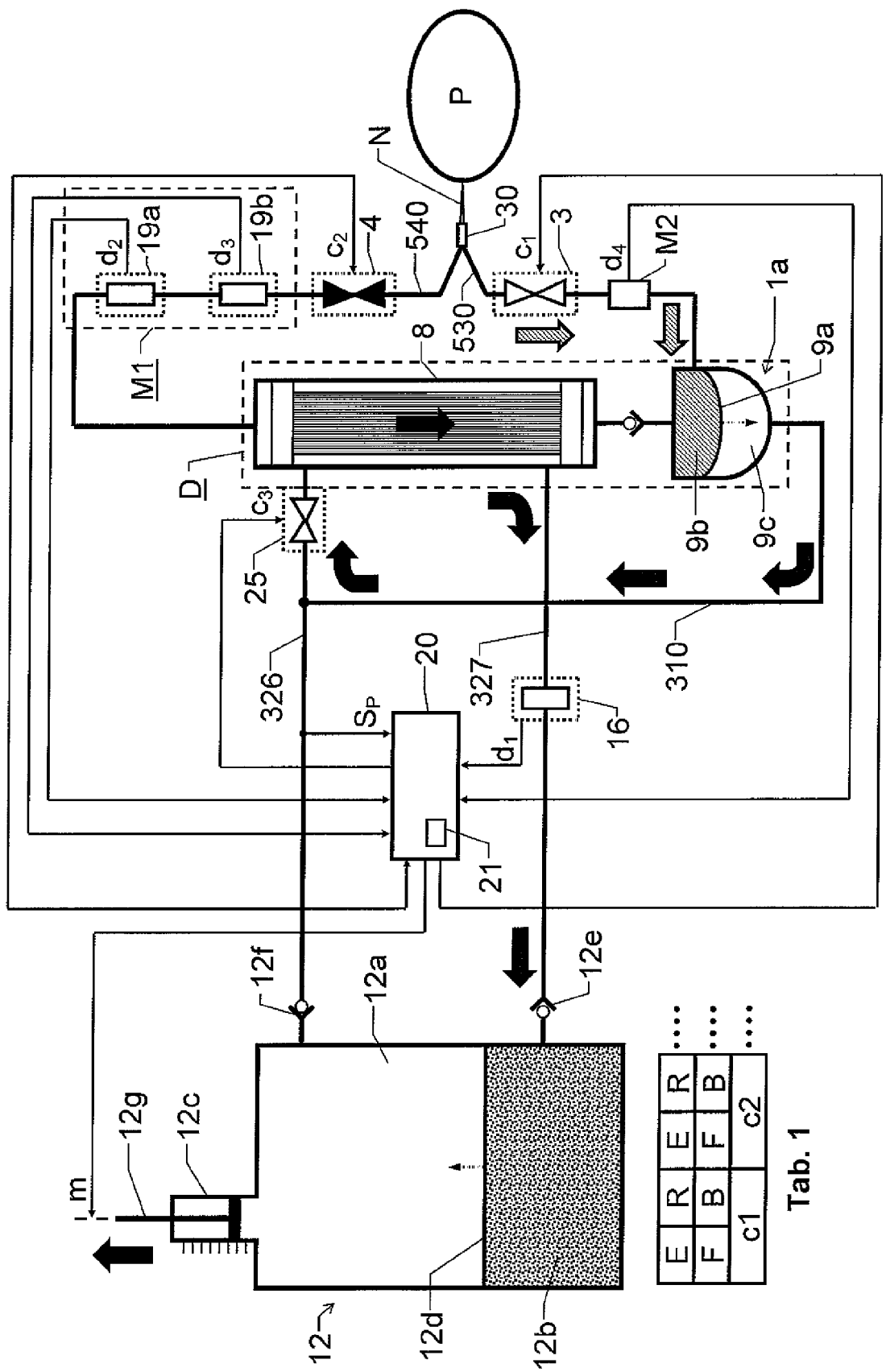
FIG. 1a shows a block diagram over a blood treatment apparatus according to a first embodiment of the invention during a first phase of a cyclic treatment process.

We refer initially to FIG. 1a, which shows a block diagram over a blood treatment apparatus (e.g. a dialysis apparatus) according to a first embodiment of the invention during a first phase of a cyclic process.

The apparatus includes a blood treatment unit 8 (typically represented by a dialyzer), a reciprocal fluid pump 12c and a blood pump 1a. The fluid pump 12c is configured to pass a blood treatment fluid (e.g. dialysis fluid) from a reservoir compartment 12a of a rigid fluid container 12 through the blood treatment unit 8, however via the blood pump 1a. The blood pump 1a is further configured to extract untreated blood from a blood source, here represented by a patient P; pass the extracted blood through the blood treatment unit 8 and deliver treated blood to a target vessel, here again represented by the patient P. According to the invention, the fluid pump 12c is configured to control the operation of the blood pump 1a via the blood treatment fluid. Moreover, the blood pump 1a is integrated into a joint apparatus element D that includes the blood treatment unit 8.

In order to control the operation of the blood pump 1a by means of the fluid pump 12c, the blood pump 1a has a pumping chamber, which is separated into first and second accumulation containers 9b and 9c respectively. Further, a flexible member 9a (e.g. in the form of a soft/elastic membrane) constitutes a separation wall between the first and second accumulation containers 9b and 9c.

The flexible member 9a is movable within the pumping chamber so as to vary a volume relationship between the first and second accumulation containers 9b and 9c. The first accumulation container 9b is configured to receive an amount of untreated blood from the patient P, and the second accumulation container 9c is configured to receive an amount of fresh blood treatment fluid from the fluid container 12. Hence, the blood treatment fluid may act on the blood with the flexible member 9a as a separating interface. Consequently, the blood treatment fluid can be used as a working medium for pumping blood, i.e. extract blood from the patient P, pass the extracted blood through the blood treatment unit 8, and return treated blood to the patient P.

To enable a desired operation of the blood treatment apparatus, the apparatus includes first and second blood valve means 3 and 4 respectively. The first blood valve means 3 is configured to control the extraction of untreated blood from the patient P via a needle N, and the second blood valve means 4 is configured to control the return of treated blood to the patient P, likewise via the needle N. The blood valve means 3 and 4 need to be activated alternately, such that the first blood valve means 3 is open while the second blood valve 4 is closed, and vice versa.

Moreover, the blood pump 1a and the fluid pump 12c are controlled according to a cyclic process, wherein the operation cycles of the fluid pump 12c and the blood pump 1a are synchronized. This means that, during a first phase the blood pump 1a receives blood contemporaneous with the fluid pump 12c performing a first pump action (here, moving a piston element 12g outwards to suck fresh blood treatment fluid out from the second accumulation container 9c). During a second phase (illustrated in FIG. 1b), subsequent to the above-mentioned first phase, the fluid pump 12c performs a second pump action (here, moves the piston element 12g inwards to push fresh blood treatment fluid into the second accumulation container 9c) while the blood pump 1a ejects untreated blood into the blood treatment unit 8. The fresh blood treatment fluid leaves the fluid container 12 via a non-return valve 12f.

To achieve this function, the first and second blood valve means 3 and 4 are controlled in coordination with the operation of the fluid pump 12c. Furthermore, in course of the process (i.e. extracting untreated blood from the blood source/patient P and delivering treated blood to the target vessel/patient P), it is desirable that the blood pressure be monitored. To this aim, it is preferable if the blood treatment apparatus includes at least one pressure measuring means.

Figure 1B:
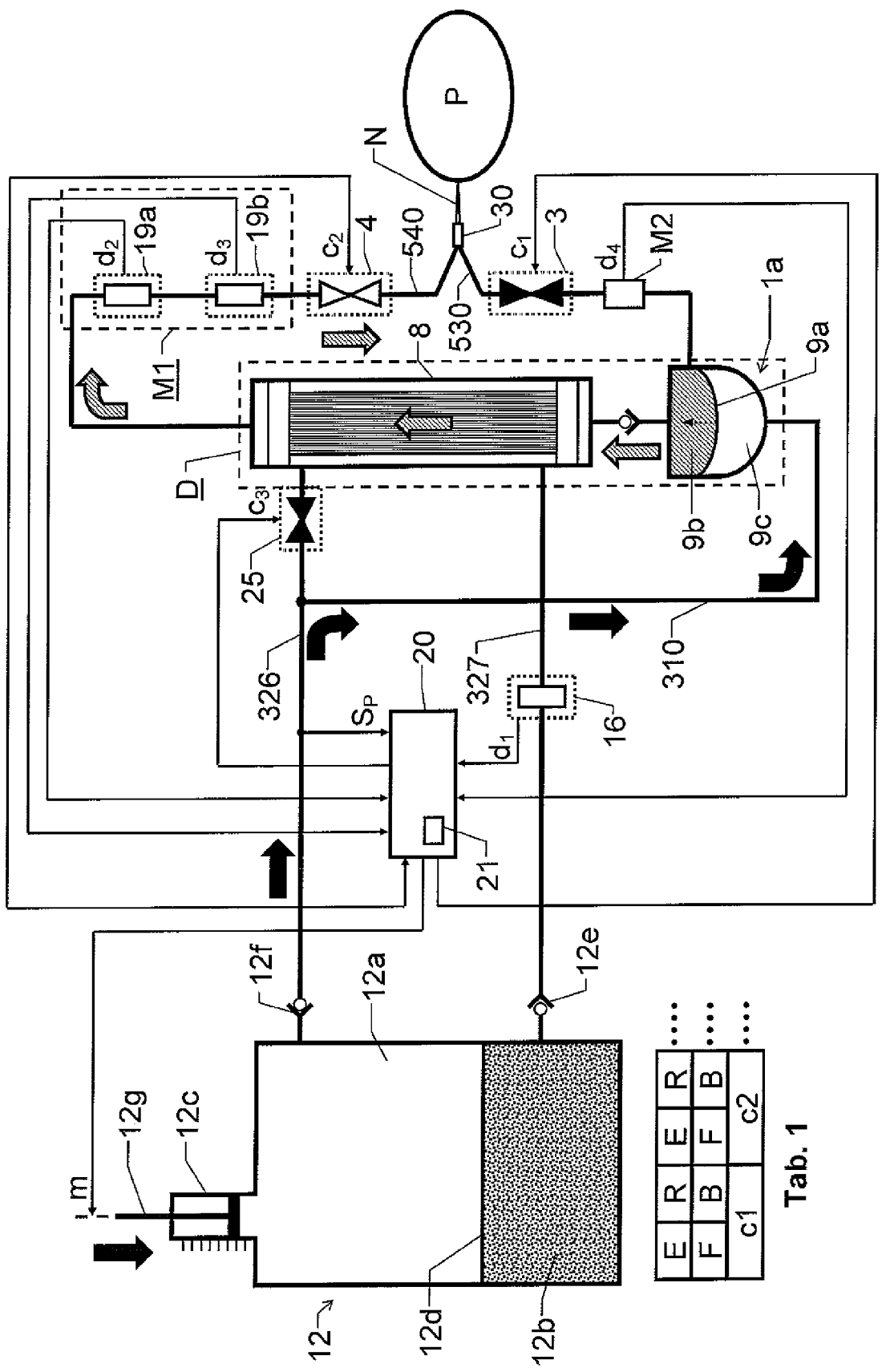
FIG. 1b shows the block diagram over the blood treatment apparatus according to the first embodiment of the invention during a second phase of the cyclic process.

In the embodiment of the invention illustrated in FIGS. 1a and 1b, first and second pressure parameters are measured via a pressure sensor signal $S_P$, which is registered on a conduit configured to pass fresh blood treatment fluid from the fluid container 12a to the blood treatment unit 8. For reasons of simplicity, we here assume that a pressure measuring unit is included in a control unit 20. In any case, the pressure measuring unit does not come into contact with the blood. Instead, the blood pressure is measured via the blood treatment fluid, which due to the contact with the flexible member 9a has a pressure level equal to that of the blood. Specifically, the first pressure parameter represents a first pressure level of the untreated blood extracted from the patient P, and the second pressure parameter represents a second pressure level of the treated blood being returned to the patient P. Additionally, the first and second pressure parameters are registered at different points in time. Therefore, a single pressure measuring means is sufficient to determine both parameters. It is worth mentioning, though, that the second pressure parameter is measured over the blood treatment unit 8.

FIG. 1a illustrates a first phase of a cyclic process during which untreated blood is extracted from the patient P. Thus, the first blood valve means 3 is open and the second blood valve 4 is closed. The fluid pump 12c also performs a pump action wherein its piston element 12g moves outwards. As a result, fresh blood treatment fluid is sucked out from the second accumulation container 9c, and the blood volume in the first accumulation container 9b increases. Therefore, the first phase may also be referred to as the blood extraction phase, denoted E in Table 1. Analogously, the second phase illustrated in FIG. 1b may be referred to as the blood return phase, denoted R in Table 1. Here, the first and second phases E and R complete a first cycle c1 of the process. Then follows a second cycle c2, and so on. Table 1 also shows a symbol F denoting that blood treatment fluid is passed through the blood treatment unit 8, and a symbol B denoting that blood is passed through the blood treatment unit 8. As can be seen, in this embodiment, the blood treatment fluid and the blood pass through the blood treatment unit 8 in the form of alternating flows, i.e. one separate flow in each respective phase E or R.

The used blood treatment fluid is discharged from the second accumulation container 9c via a first working fluid port into a fluid outlet conduit. After leaving the blood pump 1a, the blood treatment fluid passes the blood treatment unit 8, and continues into a waste compartment 12b of the fluid container 12 via a non-return valve 12e. Typically, in the blood treatment unit 8, the blood treatment fluid runs through a large number of hollow fibers made from semi-permeable membrane, and dialysis takes place over the semi-permeable membrane.

Here, a movable wall member 12d in the fluid container 12 separates the waste compartment 12b from the reservoir compartment 12a in such a manner that the volume of the waste compartment 12b may be gradually increased to accept a growing amount of used blood treatment fluid, and the volume of the reservoir compartment 12a may be decreased correspondingly as the fresh blood treatment fluid is consumed.

Specifically, during the first phase (the blood extraction phase E), the first blood valve means 3 is open, the second blood valve 4 is closed and the fluid valve means 25 is open. The fluid pump 12c also operates to suck fresh blood treatment fluid from the second accumulation container 9c, via the fluid valve means 25, through the blood treatment unit 8, and out from the apparatus. The decrease of the fluid amount in the blood pump 1a, in turn, draws blood from the patient P to the first accumulation container 9b. During the second phase (the blood return phase R), the first blood valve means 3 is closed, the second blood valve 4 is open and the fluid valve means 25 is closed. Additionally, the fluid pump 12c operates to pump fresh blood treatment fluid from the fluid container 12a into the second accumulation container 9c. The increasing amount of the fluid in the blood pump 1a causes the flexible member 9a to push the blood in the first accumulation container 9b through the blood treatment unit 8 and back into the patient P. When passing through the blood treatment unit 8 the blood is treated/cleaned, for instance by means of dialysis over a semi-permeable membrane. The amount of blood passing through the blood treatment unit 8 during one cycle is referred to as a stroke volume, i.e. the volume of blood taken from the patient P and brought back to the patient P during one cycle c1, c2 etc.

The blood treatment unit 8 has a fluid outlet conduit, which is configured to discharge used blood treatment fluid from the apparatus during the first phase of the cyclic process. The thus discharged fluid optionally continues into the waste compartment 12b, or down the drain.

It is further advantageous if the control unit 20, in response to the pressure sensor signal $S_P$ (expressing the first and second pressure parameters), is configured to control the first and second blood valve means 3 and 4 and the fluid valve means 25, such that the cyclic process is effected. Of course, this control also involves controlling the fluid pump 12c via a motoric signal m. Specifically, during the first phase (the blood extraction phase E), the control unit 20 is configured to generate a first control signal $c_1$ such that the first blood valve means 3 is opened, a second control signal $c_2$ such that the second blood valve means 4 is closed, and a third control signal $c_3$ such that the fluid valve means 25 is opened. Then, during the second phase (the blood return phase R), the control unit 20 is configured to generate the first control signal $c_1$ such that the first blood valve means 3 is closed, the second control signal $c_2$ such that the second blood valve means 4 is opened, and a third control signal $c_3$ such that the fluid valve means 25 is closed. Here, the control unit 20 uses the first and second pressure parameters to determine appropriate transitions between the first and second phases, and thus controlling the valve means 3, 4 and 25 and the operation of the fluid pump 12c as described above. Optionally, the control unit 20, in turn, includes, or is associated with; a memory means 21 storing computer software for controlling the control unit 20 to effect the above-described procedure.

In a start up phase (i.e. prior to initiating the above-mentioned cyclic process) the fluid circuit may be filled (or more precisely filled such that superfluous fluid rinses the circuit) with fresh blood treatment fluid (e.g. dialysis fluid) from the fluid container 12a. The filling of the fluid causes any air in the dialysis fluid circuit to be pushed back into the waste compartment 12b (or drain) where it is vented. Correspondingly, the first needle N1 may be connected to a saline solution (or other appropriate fluid) to fill and rinse, and thus eliminate any gas bubbles in the blood circuit. This process of filling and rinsing the apparatus is normally referred to as priming.

Optionally, the blood pump 1a is configured to be in fluid connection with the treatment unit 8 throughout an entire treatment of an amount of blood from the patient P. This means that a blood side of the apparatus in which the blood pump 1a is included is completely filled with blood until the treatment is completed. Consequently, the blood can be treated/cleaned efficiently.

It is further preferable that the fluid pump 12c is configured to be in fluid connection with the treatment unit 8 throughout an entire treatment of an amount of blood from the patient P. Analogously, this means that a fluid side of the apparatus in which the fluid pump 12c is included is completely filled with blood treatment fluid until the treatment is completed. Again, this vouches for an efficient treatment/cleaning of the blood.

According to one embodiment of the invention, a first blood conduit 530 is configured to be connected to the patient P (or the blood source) for receiving untreated blood, and a second blood conduit 540 is configured to be connected to the patient P (or the target vessel) for delivering treated blood. A needle connector 30 is configured to receive each of the first and second blood conduits 530 and 540 respectively. In the embodiment shown in FIGS. 1a and 1b, the single needle N, in turn, connects the needle connector 30 to the patient P.

The first blood conduit 530 may include a primary safeguard module M1, which is configured to check at least one quality parameter of the treated blood delivered to the patient P. For example, an air bubble detector 19a in the primary safeguard module M1 can be adapted to detect any undesired gas bubbles in the treated blood being delivered to the patient P, and in case a threshold value is exceeded, the air bubble detector 19a may deliver a data signal $d_2$ to the control unit 20. In response thereto, the control unit 20, in turn, optionally causes an appropriate alarm to be generated.

Alternatively, or as a complement to the above, the primary safeguard module M1 may include a priming fluid detector means 19b, which is adapted to detect if priming fluid or blood is passed through the apparatus. Hence, during the priming period, the priming fluid detector means 19b may detect when priming fluid is substituted with blood. In response thereto, the priming fluid detector means 19b is configured to deliver a data signal $d_3$ to the control unit 20. In response thereto, the control unit 20, in turn, is optionally configured to cause, trigger or indicate performance of an appropriate action.

Furthermore, the second blood conduit 530 optionally includes a secondary safeguard module M2, which is configured to check at least one quality parameter of the untreated blood received from the patient P, for instance detect the presence of gas bubbles and/or priming fluid. This renders it possible for the control unit 20 to cause generation of an alarm in response to a data signal $d_4$ from the secondary safeguard module M2, if the untreated blood is of inferior quality (e.g. due to the presence of gas bubbles caused by leakage). However, more important, if the apparatus unintentionally comes to pass blood in the opposite direction (i.e. back into the patient P via the valve means 3), the secondary safeguard module M2 may detect unwanted substances (e.g. represented by gas bubbles) in this blood, and prevent these from reaching the patient P.

Figure 2A:
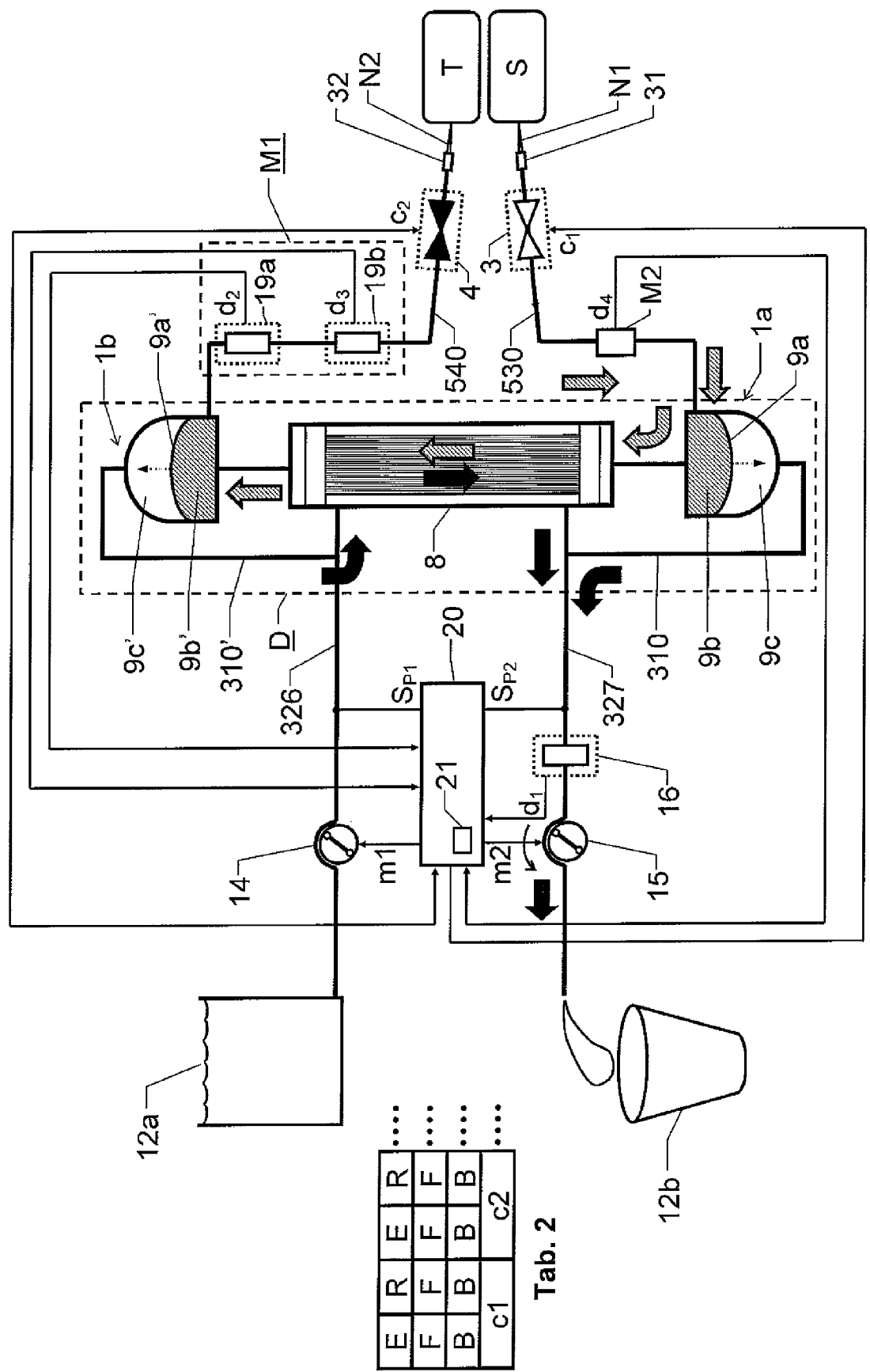
FIGS. 2a-b show block diagrams over a blood treatment apparatus according to a second embodiment of the invention during a first and a second phase respectively of a cyclic treatment process.
Figure 2B:
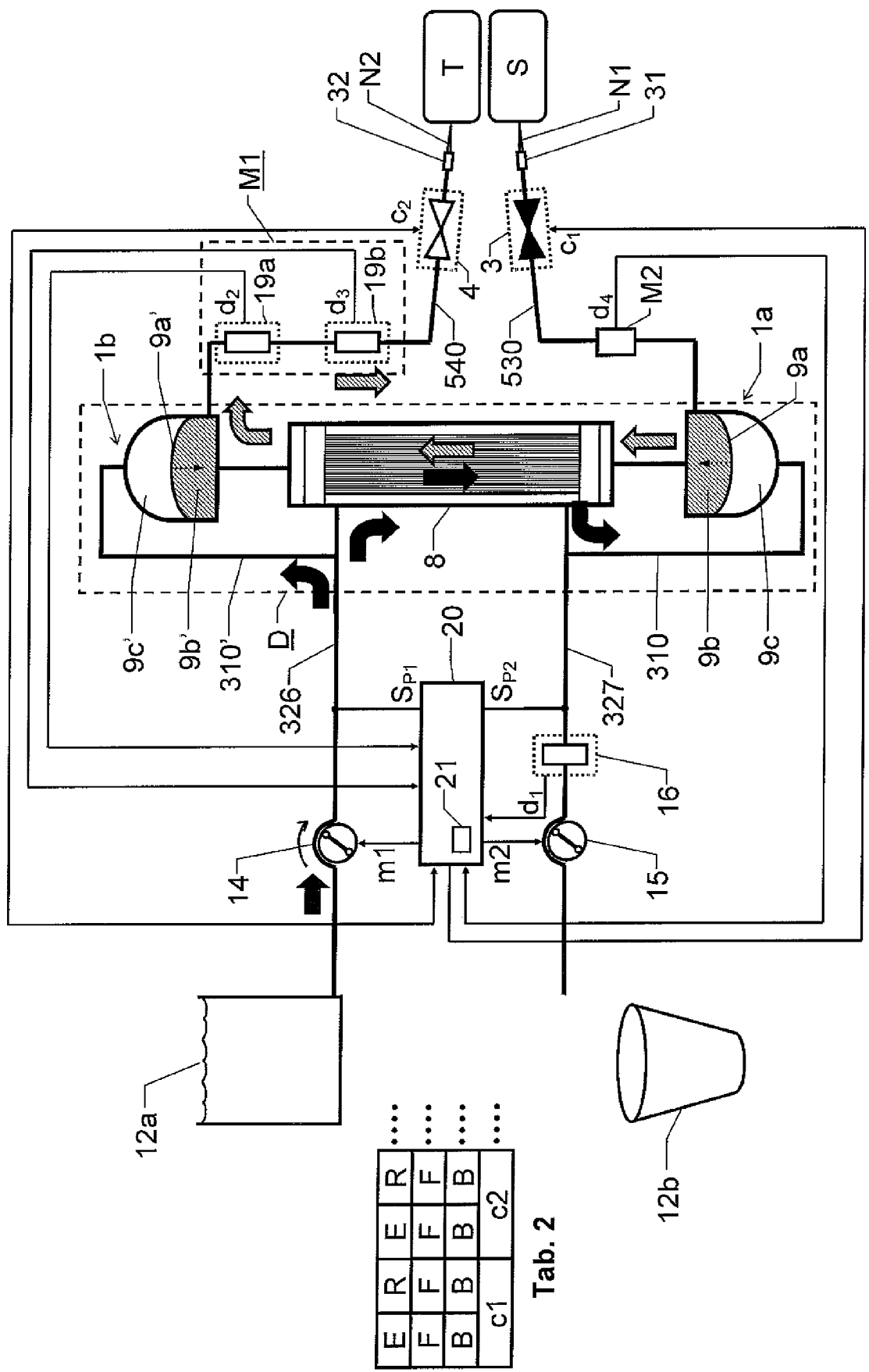

FIG. 2a shows a block diagram over a blood treatment apparatus according to a second embodiment of the invention during a first phase of a cyclic treatment process. All units and components having reference signs which also occur in FIGS. 1a and 1b designate the same units and components as those described above with reference to FIGS. 1a and 1b. To underline that fact that, according to the invention, the process of blood extraction and blood delivery need not involve a patient, FIGS. 2a and 2b illustrate a general blood source S and a general target vessel T. For example, a respective blood bag may represent the blood source S and the target vessel T. Of course, alternatively, both of these entities S and T may be represented by a patient. Consequently, it includes two needles N1 and N2 connected to the blood circuit via a respective needle connector 31 and 32.

In FIGS. 2a and 2b, the apparatus includes two blood pumps 1a and 1b respectively. Such a double-pump design is advantageous because it allows continuous flows of blood and blood treatment fluid through the blood treatment unit 8. I.e. blood and blood treatment fluid are passed through the blood treatment unit 8 both during the blood extraction phase E and the blood return phase R, as illustrated in Table 2. Naturally, this is beneficial from an efficiency point-of-view. To enable appropriate operation of this apparatus, a first pressure sensor signal $S_{P1}$ expressing the first parameter is registered on a fluid conduit delivering fresh blood treatment fluid to the blood treatment unit 8, and a second pressure sensor signal $S_{P2}$ expressing the second parameter is registered on a fluid conduit discharging used blood treatment fluid from the apparatus.

Moreover, first and second fluid pumps 14 and 15 respectively replace the reciprocal fluid pump 12c. Here, first and second motoric signals m1 and m2 from the control unit 20 control the operation of the fluid pumps 14 and 15 respectively. Specifically, during a first phase (the blood extraction phase E), the first accumulation container 9b of the blood pump 1a is charged with untreated blood from the patient P. In parallel therewith, used blood treatment fluid is discharged by means of the second fluid pump 15. Then, during a second phase (the blood return phase R, see FIG. 2b), the first fluid pump 14 pumps fresh blood treatment fluid from the fluid container 12a, through the blood treatment unit 8 and into the second accumulation container 9c of the first blood pump 1a.

In parallel therewith, blood is pushed through the blood treatment unit 8 and back to the patient P. Hence, blood and blood treatment fluid pass simultaneously through the unit 8.

Analogous to the first embodiment of the invention described above with reference to FIGS. 1*a* and 1*b*, the blood pumps 1*a* and 1*b* and/or the fluid pumps 14 and 15 are optionally configured to be in fluid connection with the blood treatment unit 8 throughout an entire treatment of an amount of blood from the patient P. Namely, this vouches for an efficient treatment/cleaning of the blood.

According to one embodiment of the invention, both the blood pumps 1*a* and 1*b* are integrated with the blood treatment unit 8 into the joint apparatus element D. Of course, this is advantageous in a self care environment because the user/patient may thereby discard the entire joint apparatus element D after completion of the treatment. This is desirable both from a handling and safety point-of-view.

FIG. 3 shows a perspective view of the proposed joint apparatus element D according to a first design alternative. This design is suitable for the apparatus according to the first embodiment of the invention described above with reference to FIGS. 1*a* and 1*b*. Here, the joint apparatus element D is configured to receive a flow of fresh blood treatment fluid FF via a fluid inlet connection 326 to the blood treatment unit 8. Used blood treatment fluid is ejected via a fluid outlet connection 327 from the blood treatment unit 8. A blood inlet connection 31 is configured to receive a flow untreated blood CS into the blood pump 1*a*, and a blood outlet connection 32 is configured to deliver treated blood from the joint apparatus element D.

FIGS. 4*a* and 4*b* show perspective views of the proposed joint apparatus element D according to a second design alternative.

This design is compatible with for example the apparatus illustrated in the above-described FIGS. 2*a* and 2*b*. Specially, FIG. 4*b* shows the joint apparatus element D in an assembled state, and FIG. 4*a* shows an exploded view of the blood pumps 1*a* and 1*b*, where inter alia the flexible members 9*a* and 9*a*' are visible. The interiors of the first blood pump's 1*a* second accumulation container 9*c* and the second blood pump's first accumulation container 9*b*' are also partially observable in FIG. 4*a*.

As can be seen in FIG. 4*b*, the joint apparatus element D includes a body module that has an essentially cylindrical outline with a central length axis (not shown), and the blood pumps 1*a* and 1*b* are arranged essentially symmetrically with respect to the central length axis at a respective end segment of the blood treatment unit 8.

As is apparent from FIGS. 2*b*, 4*a* and 4*b*, incoming fresh blood treatment fluid FF is passed both directly into the blood treatment unit 8 and into the second accumulation container 9*c*' of the second blood pump 1*b*. A conduit 310' is configured to accomplish the latter transport. Naturally, the conduit 310' is likewise configured to subsequently pass the fresh blood treatment fluid out from the second accumulation container of the second blood pump 1*b* and into the blood treatment unit 8. A first ring segment 320 around the periphery of the element D is configured to distribute a flow of incoming fresh blood treatment fluid FF over the blood treatment unit 8. The first ring segment 320 is likewise configured to supply fresh blood treatment fluid to and receive fresh blood treatment fluid from the second accumulation container 9*c*' via the conduit 310'.

As is further apparent from FIG. 2*a*, a flow of used blood treatment fluid is ejected both from the blood treatment unit 8 and from the first blood pump 1*a* via a conduit 310. These flows exit as a combined flow UF of used blood treatment fluid from the joint apparatus element D. Naturally, analogous to the conduit 310', the conduit 310 is also configured to pass the used blood treatment fluid in the opposite direction, i.e. into the second accumulation container 9*c* of the first blood pump 1*a*. A second ring segment 325 around the periphery of the element D is configured to collect used blood treatment fluid to be ejected from the blood treatment unit 8. The conduit 310 is connected to the second ring segment 325. However, this conduit is not visible in FIG. 4*a* or 4*b*.

A first blood connector 31 is configured to receive a flow of untreated blood CS from a blood source S, P; and a second blood connector 32 is configured to deliver a flow of treated blood CT to a target vessel T, P.

FIG. 4*a* shows grooves G on the inner surfaces of the pump chambers which grooves G are configured to prevent the flexible members 9*a* and 9*a*' in the blood pumps 1*a* and 1*b* respectively to be sucked into a locked position against the inner walls of the pump chambers in the end positions for the flexible members 9*a* and 9*a*'.

FIGS. 5*a* and 5*b* show perspective views of the proposed joint apparatus element D according to a second embodiment of the invention. FIG. 8 shows a block diagram over an apparatus into which the second embodiment of the invention can be fitted.

As can be seen, in contrast to the embodiment shown in FIGS. 2*a* and 2*b*, there is here a fluid connection 311 between the first blood pump 1*a* and a fluid inlet connection 326 to the blood treatment unit 8. Moreover, an outlet fluid connection 327 from the blood treatment unit 8 is connected to the second blood pump 1*b* via a connection 311'.

In FIG. 5*a*, this cross-connection is represented by first and second fluid channels 410 and 420 respectively along the body of the joint apparatus element D. FIG. 4*a* also shows a lid element 430 configured to seal the channels 410 and 420. FIG. 5*b* depicts the joint apparatus element D when the lid element 430 is attached.

The cross-connection illustrated in FIGS. 5*a* and 5*b* is advantageous because it renders it a relatively straightforward task to synchronize the blood pumps 1*a* and 1*b*. Namely, these components are thereby arranged in a balanced configuration. By synchronized, we mean that the flexible members 9*a* and 9*a*' of the blood pumps 1*a* and 1*b* reach their respective end positions simultaneously.

Analogous to the second embodiment discussed above, FIGS. 5*a* and 5*b* show a joint apparatus element D including a body module that has an essentially cylindrical outline with a central length axis (not shown). Moreover, the blood pumps 1*a* and 1*b* are here arranged essentially symmetrically with respect to the central length axis at a respective end segment of the blood treatment unit 8.

A first fluid connection 326 is configured to receive a flow of fresh blood treatment fluid FF, and a second fluid connection 327 is configured to output a flow of used blood treatment fluid UF. Analogous to the first embodiment of the invention, the blood pumps 1*a* and 1*b* are arranged at a respective end segment of the joint apparatus element D. Here, however, the first blood pump 1*a* is configured to operate based on fresh blood treatment fluid transported via a conduit 440, whereas the second blood pump 1*b* is configured to operate based on used blood treatment fluid transported via a conduit 450. In FIGS. 5*a* and 5*b*, we see a blood connection 31 configured to receive a flow of untreated blood CS from a blood source S, P. However, the corresponding connection 32 that is configured to deliver a flow of treated blood to a target vessel T, P is not visible here.

FIGS. 6a to 6f show perspective views of the proposed joint apparatus element according to a fourth design alternative, which is compatible with the apparatus illustrated in FIGS. 2a and 2b.

Similar to the designs illustrated in FIGS. 3, 4a, 4b, 5a and 5b, FIGS. 6a through 6f show a joint apparatus element D including a body module that has an essentially cylindrical outline with a central length axis. However, In contrast to FIGS. 3, 4a, 4b, 5a and 5b, in the design of FIGS. 6a through 6f the blood pumps 1a and 1b are arranged on a side surface of the blood treatment unit 8, such that the at least one blood pump 1a and 1b are located essentially asymmetrically with respect to the central length axis of the body module.

Here, FIG. 6a shows a first lid element 505; FIG. 6b shows the flexible members 9a and 9a' of the first and second blood pumps 1a and 1b respectively; FIG. 6c shows a backbone structure 525 and conduits 530 and 540 configured to receive and deliver blood respectively; FIG. 6d shows a second lid element 515 configured to seal the backbone structure 525; and FIG. 6e shows the blood treatment unit 8 and its fluid connections 326 and 327 having a blood outlet 51 and a blood inlet 52 respectively to the backbone structure 525.

FIG. 6b shows grooves G in the accumulation container configured to hold blood 9b, 9b'. Corresponding grooves G also exist in the accumulation container configured to hold blood treatment fluid 9c, 9c'. These grooves G are configured to prevent the flexible members 9a and 9a' to be sucked into a locked position against the inner walls of the pump chambers Ca and Cb in the end positions for the flexible members 9a and 9a'.

The first lid element 505 contains a conduit 510 configured to pass fresh blood treatment fluid into and out from the second accumulation container of the second blood pump 1b (cf. the above-described conduit 310), and a conduit 520 configured to pass fresh blood treatment fluid into and out from the second accumulation container of the first blood pump 1a (cf. the above-described conduit 320).

In addition to blood and fluid channels, the backbone structure 525 includes inter alia a first pumping chamber Ca in which the flexible member 9a of the first blood pump 1a is mounted, and a second pumping chamber Cb in which the flexible member 9a' of the second blood pump 1b is mounted.

FIG. 6f shows the joint apparatus element D in an assembled state. For instance, here we see the first and second blood pumps 1a and 1b respectively, a first fluid connection 326 configured to receive a flow of fresh dialysis fluid FF, a second fluid connection 327 configured to output a flow of used dialysis fluid UF, the conduit 530 configured to receive an input flow CS of untreated blood from the blood source S, P and the conduit 540 configured to deliver an output flow CT of treated blood to the target vessel T, P. Additionally, FIG. 6f embodies a set of ports 551, 552 and 553, which may be used for auxiliary purposes, such as infusion of anticoagulant substances and/or drugs and/or for taking blood samples.

FIG. 7 shows a perspective view of the proposed joint apparatus element according to a fourth embodiment of the invention. Here, all units, components and ports having reference signs, which also occur in FIG. 6f designate the same units and components as those described above with reference to FIG. 6f. In contrast to FIG. 6f, FIG. 7 depicts four ports 326, 326', 327 and 327' respectively configured to handle blood treatment fluid.

Such a design is required in order to enable the fluid pumps 14 and 15 to be included in the fluid paths between the blood pumps 1a and 1b and the blood treatment unit 8, and thereby not necessarily disposable.

FIG. 9a shows a block diagram over an apparatus similar to the one shown in FIG. 8, however in this apparatus the second accumulation container 9c' of the second blood pump 1b is provided with an inlet for working fluid that is separate from an outlet for the working fluid. The features in FIG. 9a have reference signs that correspond to those used in connection with FIG. 8.

FIG. 9b shows a block diagram over an apparatus similar to the one shown in FIG. 9a, however in this apparatus also the second accumulation container 9c of the first blood pump 1a is provided with an outlet separate from the inlet.

One advantage with separating the outlet from the inlet is that identification of when the membrane in the blood pump 1a, 1b reaches its respective end position, and thereby synchronization of the apparatus, is simplified.

The separated inlet and outlet in the second accumulation container 9c, 9c' of the first and the second blood pump respectively may be provided in the joint apparatus element D in FIG. 6a through 6f although they are not specifically shown in these Figures.

The term "comprises/comprising" when used in this specification is taken to specify the presence of stated features, integers, steps or components. However, the term does not preclude the presence or addition of one or more additional features, integers, steps or components or groups thereof.

The reference to any prior art in this specification is not, and should not be taken as, an acknowledgement or any suggestion that the referenced prior art forms part of the common general knowledge in Australia, or in any other country.

The invention is not restricted to the described embodiments in the figures, but may be varied freely within the scope of the claims.

The invention claimed is:

1. A blood treatment apparatus, comprising:
   a blood treatment unit configured to receive untreated blood and fresh blood treatment fluid, and emit treated blood and used blood treatment fluid,
   at least one fluid pump configured to pass blood treatment fluid through the blood treatment unit, and
   at least one blood pump configured to extract untreated blood from a blood source, pass extracted blood through the blood treatment unit, and deliver treated blood to a target vessel, wherein each of the at least one blood pump comprises a pumping chamber and an impermeable flexible member separating the pumping chamber into a first accumulation container and a second accumulation container, the flexible impermeable member being movable within the pumping chamber to vary a volume relationship between the first and second accumulation containers, the second accumulation container being configured to receive an amount of the blood treatment fluid to act on the flexible impermeable member which thereby pumps blood from the first accumulation container, and the at least one fluid pump and the at least one blood pump being arranged such that the blood treatment fluid constitutes the working fluid for the at least one blood pump,
   wherein at least one of the at least one fluid pump is configured to control the operation of at least one of the at least one blood pump via the blood treatment fluid, and
   at least one of the at least one blood pump is integrated into a joint apparatus element comprising the blood treatment unit.

2. The blood treatment apparatus according to claim 1, wherein the joint apparatus element is adapted to be disposable.

3. The blood treatment apparatus according to claim 1, further comprising first and second blood pumps, said first and second blood pumps being integrated into the joint apparatus element.

4. The blood treatment apparatus according to claim 1, wherein each of the at least one blood pump is configured to be in fluid connection with the treatment unit throughout an entire treatment of an amount of blood from the blood source.

5. The blood treatment apparatus according to claim 1, wherein each of the at least one fluid pump is configured to be in fluid connection with the treatment unit throughout an entire treatment of an amount of blood from the blood source.

6. The blood treatment apparatus according to claim 1, comprising:
a first blood conduit configured to be connected to the blood source,
a second blood conduit configured to be connected to the target vessel, and
at least one needle connector configured to connect the first and second blood conduits with at least one needle.

7. The blood treatment apparatus according to claim 6, wherein the first blood conduit comprises a primary safeguard module configured to check at least one quality parameter of the treated blood delivered to the target vessel.

8. The blood treatment apparatus according to claim 7, wherein the primary safeguard module comprises an air bubble detector adapted to detect any undesired gas bubbles in the treated blood being delivered to the target vessel.

9. The blood treatment apparatus according to claim 7, wherein the primary safeguard module comprises a priming fluid detector device configured to detect if priming fluid or blood is passed through the apparatus.

10. The blood treatment apparatus according to claim 7, wherein the second blood conduit comprises a secondary safeguard module configured to check at least one quality parameter of the untreated blood received from the blood source.

11. The blood treatment apparatus according to claim 1, wherein the joint apparatus element comprises a body module having an essentially cylindrical outline with a central length axis, and at least one of the at least one blood pump in the joint apparatus element is arranged at an end segment of the blood treatment unit such that the at least one blood pump is arranged essentially-symmetrically with respect to the central length axis.

12. The blood treatment apparatus according to claim 1, wherein the joint apparatus element comprises a body module having an essentially cylindrical outline with a central length axis, and at least one of the at least one blood pump in the joint apparatus element is arranged on a side surface of the blood treatment unit such that the at least one blood pump is arranged essentially asymmetrically with respect to the central length axis.

13. The blood treatment apparatus according to claim 1, wherein at least one of the at least one blood pump in the joint apparatus element is provided with an inlet for blood treatment fluid that is separate from an outlet for the blood treatment fluid.

14. A blood treatment apparatus, comprising:
a blood treatment unit configured to receive untreated blood and fresh blood treatment fluid, treat the blood using the blood treatment fluid, and discharge treated blood and used blood treatment fluid,
a treatment fluid pump configured to move blood treatment fluid through the blood treatment unit,
an extracorporeal blood passage which is configured to receive the untreated blood from a blood source, move the untreated blood through the blood treatment unit, and deliver the treated blood to a target vessel, and
a blood pump including a first accumulation chamber, a second accumulation chamber and a flexible impermeable member separating the first and second accumulation chambers, wherein the first accumulation chamber is included in the extracorporeal blood passage, wherein a pressure applied by the treatment fluid pump to the blood treatment fluid moves the permeable flexible member and thereby moves the untreated blood in and out of the blood pump and through the extracorporeal blood passage.

15. The blood treatment apparatus according to claim 14, wherein the blood pump comprises a flexible membrane separating a pumping chamber into a second accumulation container configured to receive the blood treatment fluid and a first accumulation container configured to receive and discharge the extracted untreated blood,
the flexible membrane is displaced by the pressure applied to the blood treatment fluid in the second accumulation container and the displacement of the flexible membrane displaces the extracted untreated blood from the first accumulation container to the blood treatment unit.

16. The blood treatment apparatus according to claim 14, wherein the pressure applied to the treatment fluid displaces a flexible membrane in the blood pump and the displacement of the flexible membrane moves the untreated blood in and out of the blood pump.

17. The blood treatment apparatus according to claim 14 further comprising a first valve coupled to a blood passage between the blood source and the blood pump, and a second valve coupled to a blood passage between the blood treatment unit and the target vessel, wherein the apparatus has a blood withdrawal mode during which the first valve is opened and the second valve is closed while the treatment fluid pump reduces the pressure applied to the treatment fluid and has a blood infusion mode during which the first valve is closed and the second valve is opened while the treatment fluid pump increases the pressure applied to the treatment fluid.

* * * * *